United States Patent
Chan et al.

(10) Patent No.: US 9,332,938 B2
(45) Date of Patent: May 10, 2016

(54) FLAT LANCET IMMOBILIZATION

(75) Inventors: Frank A. Chan, Sunnyvale, CA (US); Daniel Wong, Sunnyvale, CA (US); Charles C. Raney, Camdenton, MO (US); Christopher Wiegel, Sunnyvale, CA (US); Steven N. Roe, San Mateo, CA (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1435 days.

(21) Appl. No.: 12/208,698

(22) Filed: Sep. 11, 2008

(65) Prior Publication Data

US 2009/0036797 A1 Feb. 5, 2009

Related U.S. Application Data

(63) Continuation-in-part of application No. 11/103,871, filed on Apr. 12, 2005, now Pat. No. 7,695,442, and a continuation-in-part of application No. 11/551,414, filed on Oct. 20, 2006, now Pat. No. 7,935,063, which is a continuation-in-part of application No. 11/549,302, filed on Oct. 13, 2006, now Pat. No. 7,955,271, which is a continuation-in-part of application No. 11/070,502, filed on Mar. 2, 2005, now Pat. No. 7,815,579.

(51) Int. Cl.
| | |
|---|---|
| *A61B 5/157* | (2006.01) |
| *A61B 5/15* | (2006.01) |
| *A61B 5/145* | (2006.01) |
| *A61B 5/1468* | (2006.01) |
| *A61B 5/151* | (2006.01) |
| *A61B 17/3209* | (2006.01) |
| *A61B 10/00* | (2006.01) |

(52) U.S. Cl.
CPC ............... *A61B 5/157* (2013.01); *A61B 5/1411* (2013.01); *A61B 5/1468* (2013.01); *A61B 5/14532* (2013.01); *A61B 5/15142* (2013.01); *A61B 17/32093* (2013.01); *A61B 2010/0003* (2013.01); *A61B 2562/0295* (2013.01)

(58) Field of Classification Search
CPC .... A61B 5/150534–5/150725; A61B 5/15186; A61B 5/150412; A61B 5/157; A61B 5/15142; B29C 66/4332
USPC ........................... 600/583, 584; 606/181, 182
See application file for complete search history.

(56) References Cited

U.S. PATENT DOCUMENTS 1,387,839 A * 8/1921 Davis ............................. 206/370
3,361,253 A * 1/1968 Lonholdt ......... A61B 17/06133
206/363

(Continued)

FOREIGN PATENT DOCUMENTS

| | | |
|---|---|---|
| CN | 101115441 A | 1/2008 |
| WO | 2006/082106 A1 | 8/2006 |

OTHER PUBLICATIONS

U.S. Appl. No. 11/103,871 Office Action mailed Jun. 26, 2009.

(Continued)

*Primary Examiner* — Adam J Eiseman
(74) *Attorney, Agent, or Firm* — Woodard, Emhardt, Moriarty, McNett & Henry LLP

(57) ABSTRACT

A lancet enclosed in a sterility sheet forms a lancet packet to maintain the sterility of the lancet and prevent the lancet from unintentionally piercing the sterility sheet prior to lancet actuation. In one form, the lancet is immobilized by hot tack welding a portion of the sterility sheet to the lancet. Alternatively, portions of the sterility sheet are hot tack welded together through an opening in the lancet to limit movement of the lancet.

21 Claims, 14 Drawing Sheets

(56) References Cited

U.S. PATENT DOCUMENTS

| | | | |
|---|---|---|---|
| 5,096,518 A * | 3/1992 | Fujikawa et al. | 156/89.28 |
| 5,397,334 A | 3/1995 | Schenk et al. | |
| 5,514,152 A | 5/1996 | Smith | |
| 5,599,351 A | 2/1997 | Haber et al. | |
| 5,779,724 A | 7/1998 | Werner | |
| 6,315,738 B1 * | 11/2001 | Nishikawa et al. | 600/583 |
| 8,007,445 B2 * | 8/2011 | Harttig | A61B 5/1411 600/583 |
| 2003/0024811 A1 | 2/2003 | Davies et al. | |
| 2003/0060730 A1 | 3/2003 | Perez | |
| 2003/0083686 A1 * | 5/2003 | Freeman et al. | 606/181 |
| 2003/0144608 A1 * | 7/2003 | Kojima et al. | 600/583 |
| 2003/0153939 A1 * | 8/2003 | Fritz et al. | 606/181 |
| 2003/0211619 A1 * | 11/2003 | Olson et al. | 436/44 |
| 2004/0064068 A1 * | 4/2004 | DeNuzzio et al. | 600/583 |
| 2004/0098008 A1 | 5/2004 | Taylor et al. | |
| 2005/0027211 A1 | 2/2005 | Kuhr et al. | |
| 2005/0036909 A1 * | 2/2005 | Erickson et al. | 422/61 |
| 2005/0232815 A1 | 10/2005 | Ruhl et al. | |
| 2005/0245954 A1 * | 11/2005 | Roe | A61B 5/1411 606/181 |
| 2005/0251064 A1 | 11/2005 | Roe | |
| 2005/0277881 A1 | 12/2005 | Sibbitt | |
| 2006/0079810 A1 | 4/2006 | Patel et al. | |
| 2006/0100543 A1 | 5/2006 | Raney et al. | |
| 2006/0200045 A1 | 9/2006 | Roe | |
| 2006/0229532 A1 | 10/2006 | Wong et al. | |
| 2007/0167869 A1 | 7/2007 | Roe | |
| 2007/0173740 A1 | 7/2007 | Chan et al. | |
| 2008/0269791 A1 * | 10/2008 | Hoenes | A61B 5/1411 606/181 |
| 2008/0300509 A1 * | 12/2008 | Hoenes et al. | 600/583 |
| 2010/0222799 A1 * | 9/2010 | Roeper et al. | 606/181 |
| 2010/0292609 A1 * | 11/2010 | Zimmer | A61B 5/1411 600/583 |

OTHER PUBLICATIONS

Non-final Office Action mailed Dec. 30, 2009, in related U.S. Appl. No. 11/549,302, filed Oct. 13, 2006 to Roe et al.

International Patent Application No. PCT/EP2009/006508 International Preliminary Report on Patentability and Written Opinion mailed Mar. 24, 2011.

U.S. Appl. No. 11/549,302 to Roe et al., Office Action mailed Jun. 25, 2010.

* cited by examiner

FLAT LANCET IMMOBILIZATION

CROSS REFERENCE TO RELATED APPLICATIONS

This application is a continuation-in-part of U.S. patent application Ser. No. 11/103,871, filed Apr. 12, 2005, now U.S. Pat. No. 7,695,442 entitled "INTEGRATED LANCING TEST STRIP WITH RETRACTABLE LANCET" which is hereby incorporated by reference in its entirety. This application is a continuation-in-part of U.S. patent application Ser. No. 11/551,414, filed Oct. 20, 2006, now U.S. Pat. No. 7,935,063 entitled "SYSTEM AND METHOD FOR BREAKING A STERILITY SEAL TO ENGAGE A LANCET", which is a continuation-in-part of U.S. patent application Ser. No. 11/549,302, filed Oct. 13, 2006, now U.S. Pat. No. 7,955,271 entitled "TAPE TRANSPORT LANCE SAMPLER", which is a continuation-in-part of U.S. patent application Ser. No. 11/070,502, filed Mar. 2, 2005, now U.S. Pat. No. 7,815,579 entitled "DYNAMIC INTEGRATED LANCING TEST STRIP WITH STERILITY COVER", which are hereby incorporated by reference in their entireties.

BACKGROUND

The present application generally concerns the field of lancing, and specifically concerns maintaining sterility of a lancet prior to use without impeding mobility of the lancet during actuation of the lancet.

Integrated disposable devices have been proposed in which a lancet is sealed behind a sterility barrier. A difficulty resulting from a lancet sealed behind a sterility barrier is damage to the sterility barrier such that the lancet is exposed. For example, if a lancet is not immobilized then it may unintentionally move and damage and/or puncture the sterility barrier. A damaged sterility barrier may not maintain the sterility of the lancet. A user lanced with a contaminated lancet could lead to infection of the user. Further, the test results from a contaminated lancet may not be accurate which could lead to many problems, mainly that of inadequate healthcare for the user.

Other integrated disposable devices have been proposed in which the lancet is sealed within a protective packet, for example, by a jointing technique to form a lancet packet. In some forms, the lancet packet is attached to a test strip to form a biosensor. One jointing technique includes positioning the lancet between a top layer of material and a bottom layer material and sealing the layers around the lancet with adhesive tape to form a lancet packet. As another example, a second jointing technique includes sandwiching the lancet between a pair of adhesive coated foils in which the coated foils are heat sealed together to form a lancet packet. In either jointing technique, excess adhesive often adheres the lancet to the foils or layers which can impede or impair mobility of the lancet during the lancing process. In other words, the lancet is stuck to one or both layers and most likely not properly driven into a user's skin to form an adequate incision in which a bodily fluid sample can be obtained. Additionally, the adhesive tape and/or the adhesive coated foils increase the overall thickness of the lancet packet and similarly decrease the number of lancet packets that can be stacked in a diagnostic structure. Moreover, mechanical devices used to apply the adhesive tape between the layers of packets and the blades or punching tools used to cut and shape the lancet packets require periodic cleaning to remove excess adhesive from the mechanical devices, blades, and/or punching tools.

Thus, there is a need for improvement in this field.

SUMMARY

In one embodiment, immobilization of the lancet within a lancet packet is achieved by tack welding a portion of top foil to the lancet to form the lancet packet. In another embodiment, immobilization of the lancet within the lancet packet occurs by tack welding opposing sheets of cover foil together through an engagement opening in the lancet. For example, the opposing sheets are pinched or pulled through the engagement opening of the lancet and melted together to form a tack weld.

In a second embodiment, the lancet is immobilized by a disengageable connection between the lancet and a spacer such that the lancet can be disengaged from the spacer when the lancet is actuated and the lancet can re-engage the spacer after use by moving the lancet back to its original position with the spacer to immobilize the lancet again. In one form, the lancet defines a receiving end configured to mate with the spacer having a male end. In another form, the lancet includes a male end configured to mate with the spacer defining a receiving end.

In another embodiment, the lancet packet is attached to a test element to form a flat biosensor. Unimpeded movement of the lancet is beneficial for integration of the lancet packets to test strips to avoid potentially wasting a test strip when movement of a corresponding lancet is impeded and an inadequate body fluid sample is obtained from this misfired lancet. Further, unimpeded movement of the lancet is also beneficial in diagnostic structures, such as cartridges, cassettes, meters, or the like, where the lancet may not be readily accessible to the user after it has been loaded in the diagnostic structure.

Further forms, objects, features, aspects, benefits, advantages, and embodiments of the present invention will become apparent from a detailed description and drawings provided herewith.

DESCRIPTION OF SELECTED EMBODIMENTS

Figure 1:
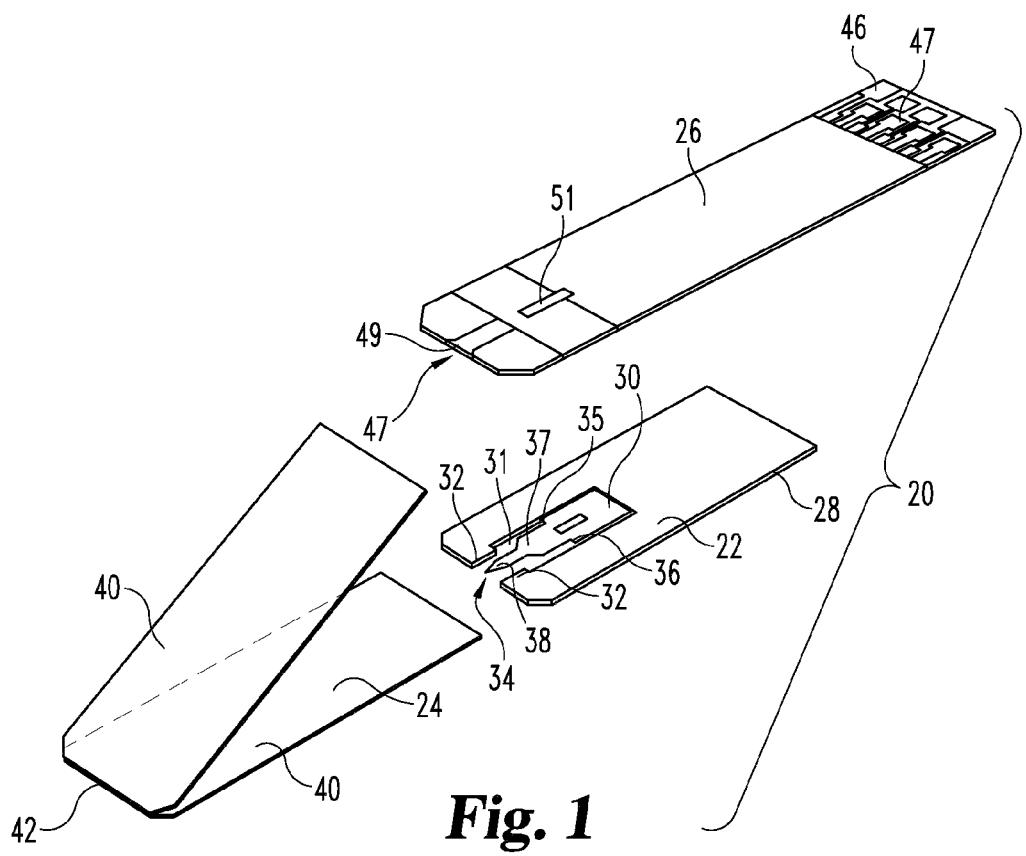
FIG. 1 is a first top exploded view of an integrated lancing test strip according to one embodiment.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments and any further applications of the principles of the invention as described herein are contemplated as would normally occur to one skilled in the art to which the invention relates.

Any directional references in this detailed description with respect to the Figures, such as up or down, or top or bottom, are intended for convenience of description, and by itself does not limit the present invention or any of its components to any particular positional or spatial orientation.

As previously discussed, one difficulty associated with integrated disposable devices includes sealing a lancet behind a sterility barrier such that movement of the lancet is restrained or limited until the lancet is actuated. If the lancet is mobile while sealed behind the sterility barrier, then the lancet may unintentionally move and pierce the sterility barrier. The exposed lancet may then become contaminated which could lead to infection of the user or, the exposed lancet may become damaged which could cause injury to the user in addition to potential infection. Moreover, the test results from a non-sterile or damaged lancet may not be accurate which could lead to many problems, mainly that of inadequate healthcare for the user. The immobilization of the lancet within the lancet packet prevents the lancet from piercing the sterility sheet before an operator is ready to use the lancet. Therefore, the sterility of the lancet is maintained and potential injury to the operator or other persons is prevented as well as damage to the lancet. The inventors discovered unique immobilization systems for limiting movement of a lancet to maintain sterility of the lancet within the lancet packet and to provide unimpeded movement of the lancet upon actuation of the lancet. In one form, a lancet is at least partially enclosed by a sterility sheet, which maintains sterility of the lancet tip to form a lancet packet. In one embodiment, the movement of the lancet within the lancet packet is limited by adhering or hot tack welding a portion of the sterility sheet to the lancet. In another embodiment, the movement of the lancet within the lancet packet is limited by hot tack welding a pair of opposing cover foils or sterility sheets together through an opening in the lancet to limit the movement of the lancet. In yet another embodiment, the movement of the lancet is limited by attaching the lancet to a spacer to form a locking mechanism. For example, the locking mechanism is configured to release the lancet from the spacer and to reattach the lancet to the spacer after a lancing event. In other embodiments, the movement of the lancet is limited by a combination of the locking mechanism and hot tack welding the sterility sheet to the lancet. In some embodiments, the lancet packet and/or lancet and spacer are attached to a test strip to form an integrated disposable.

An integrated lancing test strip or integrated disposable 20 according to one embodiment, among many, will be described initially with reference to FIGS. 1, 2, 3, 4, and 5. Referring to FIG. 1, the integrated lancing test strip 20 includes a lancet assembly or incision forming member 22 for forming an incision in tissue, a sterility sheet or foil 24 for maintaining the sterility of the lancet 22, and a test strip or biosensor 26 for acquiring a body fluid from the incision. Both the lancet 22 and the test strip 26 in the illustrated embodiment are generally flat such that the integrated lancing test strip 20 has an overall flat appearance. By being flat, multiple integrated lancing test strips 20 can be incorporated into magazines, cassettes, drums, cartridges, and the like, which allows a plurality of integrated lancing test strips 20 to be used without the need to individually load and/or dispose of used integrated devices 20. For example, the overall flat shape allows multiple integrated lancing test strips 20 to be stacked upon one another in a magazine or rolled around a reel in a cassette. Furthermore, the overall flat shape allows the integrated lancing test strip 20 to be manufactured with a continuous process in which layers of component materials can be layered to form contiguous strips of integrated lancing test strips 20 that can be cut to form individual units or remain attached for use in cassettes and the like. It should nonetheless be recognized that the integrated lancing test strip 20 in other embodiments can have a different overall shape.

Figure 5:
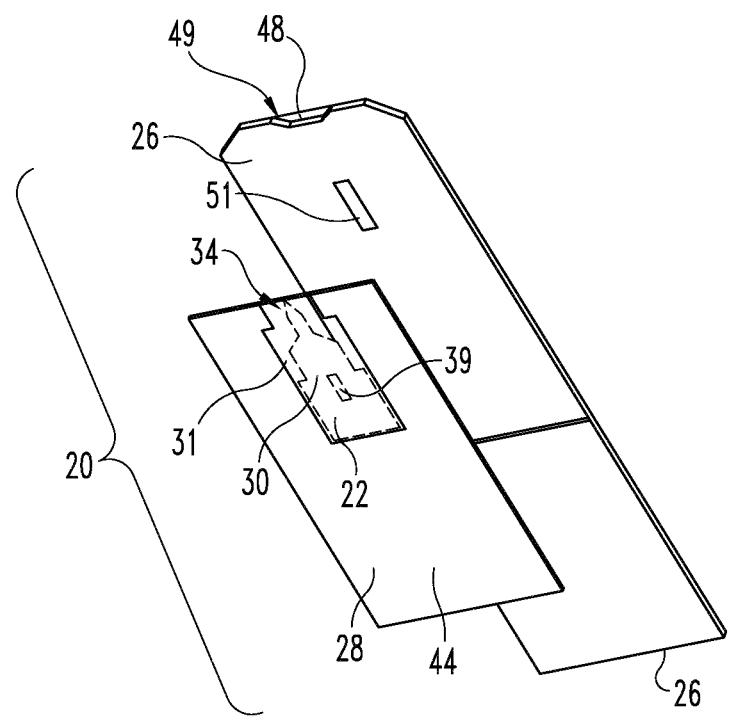
FIG. 5 is a bottom exploded view of the FIG. 1 integrated lancing test strip.

As can be seen in FIGS. 1 and 5, the lancet assembly 22 has a retaining element or guide member 28 that at least in part helps to guide a piercing member or lancet 30 during lancing. The lancet 30 is slidably retained within a guide slot or opening 31 that is defined in the retainer 28. In the course of lancing, the guide slot 31 guides the movement of the lancet 30 during both extension and retraction. In the illustrated embodiment, the lancet 30 and the retainer 28 are separate components that are not directly attached to one another. In other embodiments, as described in more detail below, the lancet is disengageably attached to the retainer or spacer. For example, a body portion of the lancet defines a receiving or female end configured to mate with a retainer or spacer having a pin or male end to retain or lock the lancet with the spacer. In another example described below, the body portion of the lancet includes a pin or male end configured to mate with the retainer defining a receiving or female end to retain the lancet with the spacer. In yet another embodiment described below, the body portion of the lancet includes a pair of protruding sides and the spacer includes a pair of legs, each leg defining a recess sized to receive one of the protruding sides to retain the lancet with the spacer.

In the illustrated embodiment, end stops 32 of the retainer 28 extend inwardly at a slot opening 34 of the guide slot 31 so as to limit the movement of the lancet 30, thereby retaining the lancet 30 in the guide slot 31. In other embodiments, the retainer has a different shape and does not include end stops. The lancet 30 has a body portion 35 with one or more stop edges 36, which are wider than the slot opening 34. When the lancet 30 is fully extended, the stop edges 36 of the lancet 30 can contact the end stops 32, and thus limit the travel of the lancet 30. However, in other embodiments, the firing mechanism, which is used to fire the lancet 30, limits the travel of the lancet 30. A neck portion 37 of the lancet 30, which is slightly smaller than the size of the slot opening 34, extends from the body portion 35 of the lancet 30. During extension of the lancet 30, the neck 37 is received between the end stops 32 such that the end stops 32 can limit undesirable rotation of the lancet 30 as the tissue is punctured. It should be noted that the sterility sheet 24 helps to constrain out-of-plane rotation of the lancet. In one form, the lancet 30 is 1 mil thinner than the retainer 28 so as to minimize friction during actuation, but of course, the dimensions can vary in other embodiments. Extending from the neck 37, the lancet 30 has a blade portion or tip 38 that is configured to cut tissue. In the illustrated embodiment, the lancet 30 defines an engagement notch or opening 39 for coupling the lancet 30 to a firing mechanism. In one form, the lancet assembly 22 is made at least in part of medical grade stainless steel, but it should be recognized that the lancet assembly 22 can be made of other materials, such as ceramics and/or plastics. Furthermore, it is contemplated that the guide member 28 and the lancet 30 can be made of different materials and/or manufactured separately. In one embodiment, the guide member 28 and lancet 30 are formed by a photo-etching technique in which a sheet of metal is photo-etched to form both the guide member 28 and the lancet 30, and in another embodiment, the lancet assembly 22 is manufactured via stamping. In another embodiment, the retainer 28 is stamped from a plastic sheet via a rotary die, and the lancet 30 is made from metal. The lancet assembly 22 in still other embodiments can be manufactured through other techniques.

Figure 2:
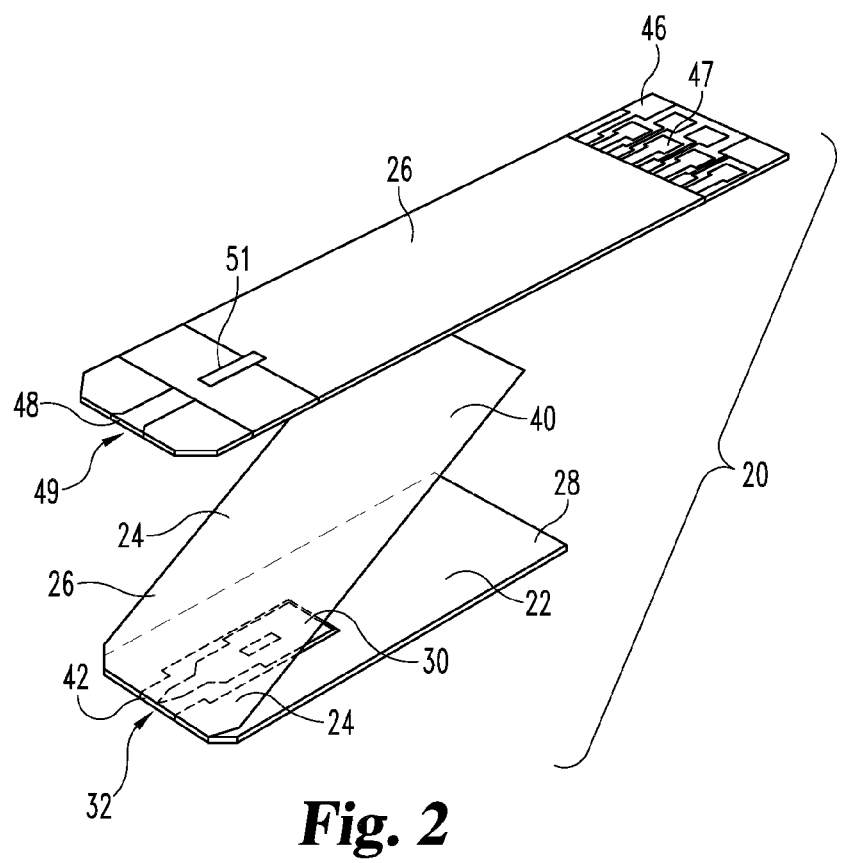
FIG. 2 is a second top exploded view of the FIG. 1 integrated lancing test strip.
Figure 3:
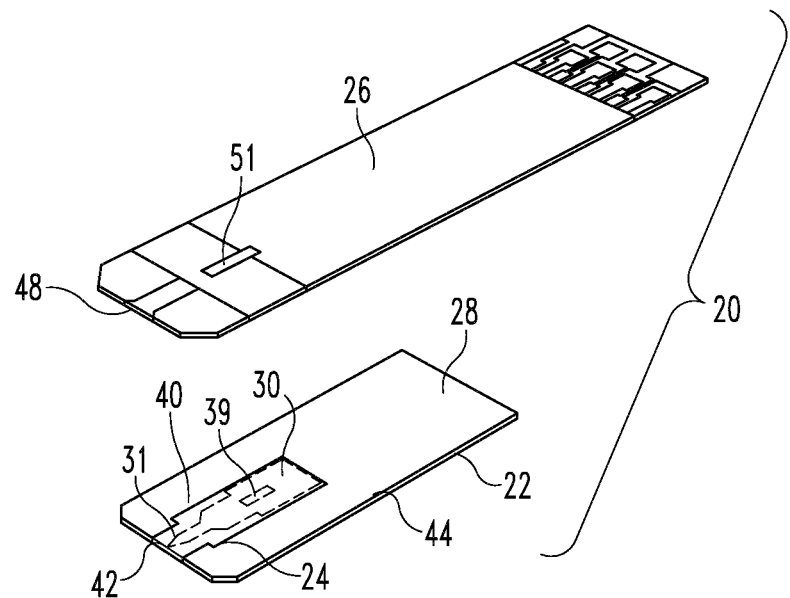
FIG. 3 is a third top exploded view of the FIG. 1 integrated lancing test strip.

With reference to FIGS. 1 and 2, after the lancet assembly 22 is formed, the lancet assembly 22 can then be packaged within the sterility sheet 24. As will be appreciated from the discussion below, the lancet assembly 22 can be packaged in the sterility sheet 24 before, during, or after the lancet assembly 22 is sterilized. In the illustrated embodiment, the sterility sheet 24 is a sheet of metallic foil, and in another embodiment, the sterility sheet 24 is made of plastic. In one particular form, the sterility sheet 24 is a 19-30 micron thick polyethylene terephthalate (PET) foil. It should be recognized that the sterility sheet 24 can be made of other types of materials and can have different dimensions. During manufacturing, the sterility sheet 24 is folded into two flaps 40 with a crease or fold 42 in between, as is shown in FIG. 1. After folding, the lancet assembly 22 in FIG. 2 is sandwiched between the two flaps 40 such that the crease 42 closes the slot opening 34 of the guide slot 31. As depicted in FIG. 3, the flaps 40 are secured to the opposite (flat) sides of the lancet assembly 22 so that the lancet 30 is sealed inside the guide slot 31 with the slot opening 34 closed by the crease 42. In one form, an adhesive is used to secure the sterility sheet to the guide member 28. Adhesive is applied on the guide member 28 around the guide slot 31 but is not applied to the lancet 30 so that the lancet 30 is able to still slide within the guide slot 31. Although an adhesive is used in the illustrated embodiment, it should be understood that the sterility sheet 24 can be sealed with the guide member 28 in other manners, such as through heat sealing or laser welding. As described in more detail below, one or both of flaps 40 can be adhered to the lancet 30 by hot tacking or melting a portion of one or both of flaps 40 onto the lancet 30 to form a tack weld. The tack weld limits movement of the lancet 30 within the guide slot 31 until the tack weld is broken. Also described in more detail below, portions of each of flaps 40 are pulled through the engagement notch or opening 39 of the lancet 30 and melted so that the melted portions of flaps 40 pull the flaps 40 together to form a tack weld and limit movement of the lancet 30 within the guide slot 31. The movement of the lancet 30 is limited until the tack weld is broken. For the sake of clarity, the drawings only show how an individual integrated lancing test strip 20 is formed, but it is contemplated that the integrated lancing test strips 20 in other embodiments are formed in a continuous process. In the continuous process, the sterility sheet 24 is a continuous band that is rolled off a reel and folded around a continuous band or belt of lancet assemblies 22 that are likewise rolled from a reel. In one variation, the lancet assemblies are singulated from the reel before being sealed in place.

Once joined together, the lancet assembly 22 and the sterility sheet 24 form a lancet package or packet 44. As mentioned before, the lancet assembly 22 can be sterilized before being enclosed in the sterility sheet 24. The lancet assembly 22 can be sterilized through any number of sterilization techniques as would occur to those skilled in the art, such as through chemical, heat, and/or radiation sterilization techniques, to name a few. It should be understood that all or part of the lancet assembly 22 can be sterilized. For instance, only the lancet 30 and guide slot 31 can be sterilized, if so desired. In another embodiment, the lancet assembly 22 is sterilized after the lancet assembly 22 is packaged inside the lancet package 44. In one form, a radiation sterilization technique is used once the lancet 30 is enclosed by the sterility sheet 24. With the lancet package 44, sterilization of the lancet assembly 22 can occur without exposing the test strip to the undesirable effects of lancet sterilization.

In the illustrated embodiment, the test strip 26 is an electrochemical type test strip. In one particular form, the test strip 26 includes a modified version of an ACCU-CHEK® brand test strip (Roche Diagnostics GmbH), but it is envisioned that other types of test strips can be used. For example, the test strip 26 in other embodiments can include an optical type test strip or can analyze fluid samples in other manners. At one end, the test strip 26 in the illustrated embodiment includes a connection portion 46 with electrical contacts 47 that transmit sample readings to a meter. Opposite the connection portion 46, the test strip 26 has a capillary channel 48 with a capillary opening 49 that is configured to draw a body fluid sample from an incision formed by the lancet 30 via capillary action. As should be appreciated, the test strip 26 inside the capillary channel 48 includes an analysis region that includes electrodes, such as working, counter, and reference electrodes, and reagents for analyzing the fluid sample. In one form, the connection portion 46 is connected to a meter, and the sample readings from the electrodes in the analysis region are transmitted to the meter via the electrical contacts.

Figure 4:
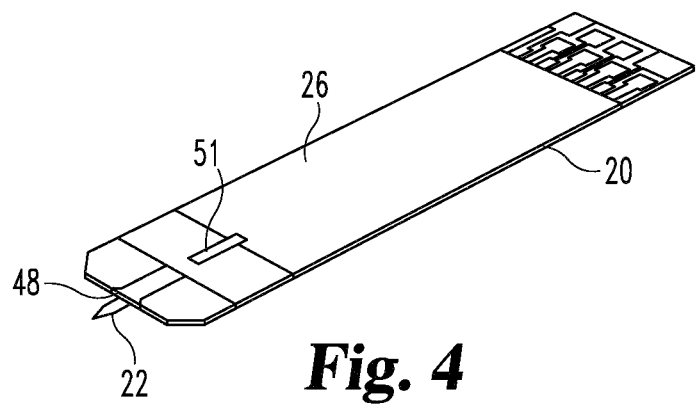
FIG. 4 is a top perspective view of the FIG. 1 integrated lancing test strip with its lancet in an extended position.

In FIGS. 3 and 4, the test strip 26 further defines a relief slot 51 through which a blade tip of a cam arm extends when engaging the lancet 30 during loading and firing. In addition, the relief slot 51 can be used to vent air from the capillary channel 48 as fluid is collected. The length of the relief slot 51 generally approximates the length of the lancing stroke of the firing mechanism used to actuate the lancet 30. When the lancet package 44 is attached to the test strip 26, the engagement notch 39 on the lancet 30 is aligned with the relief slot 51 in the test strip 26. In one embodiment, the blade tip of a cam arm for the firing mechanism extends through the engagement notch 39 of the lancet 30 as well as into the relief slot 51. When doing so, the blade tip pierces the sterility sheet 24. During lancing, the cam arm via the blade extends and retracts the lancet 30 relative to the test strip 26. As the lancet 30 extends, the tip 38 of the lancet 30 pierces the sterility sheet 24 at crease 42, as is illustrated in FIG. 4. In one form, the sterility sheet 24 at the crease 42 is weakened so as to aid in puncturing by the lancet 30, but in other forms, the crease 42 is not weakened. Once the lancet 30 is retracted back inside the guide slot 31, the two flaps 40 of the sterility sheet 24 can hold the lancet 30 inside through friction. By engaging the lancet 30 in such a manner, the risk of accidental puncturing by the integrated lancing test strip 20 is reduced because it is more difficult to manually and/or accidentally actuate the lancet 30. It should be recognized that the lancet assembly 22 can incorporate other structures for engaging the lancet 30. For instance, the engagement notch 39 in the lancet 30 can be replaced with a protrusion or knob. It is also contemplated that the lancet can be fired through non-mechanical and/or non-contact techniques which do not require the puncturing of the sterility sheet 24. As an example, the lancet 30 in another embodiment is magnetized and fired magnetically through a voice coil driver. With the lancet 30 enclosed in the sterility sheet 24 both before and after lancing, the risk of contamination is reduced, and the risk of accidental injury is likewise reduced.

Figure 6:
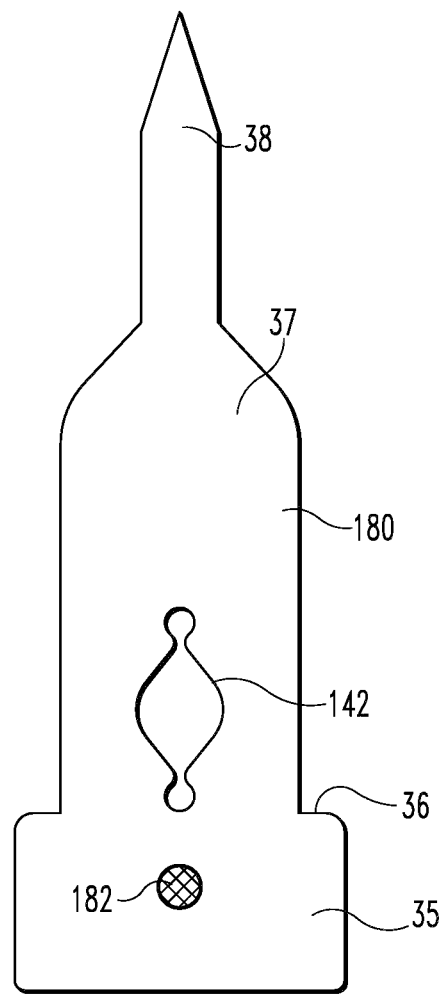
FIG. 6 is a top view of a lancet according to another embodiment.
Figure 7:
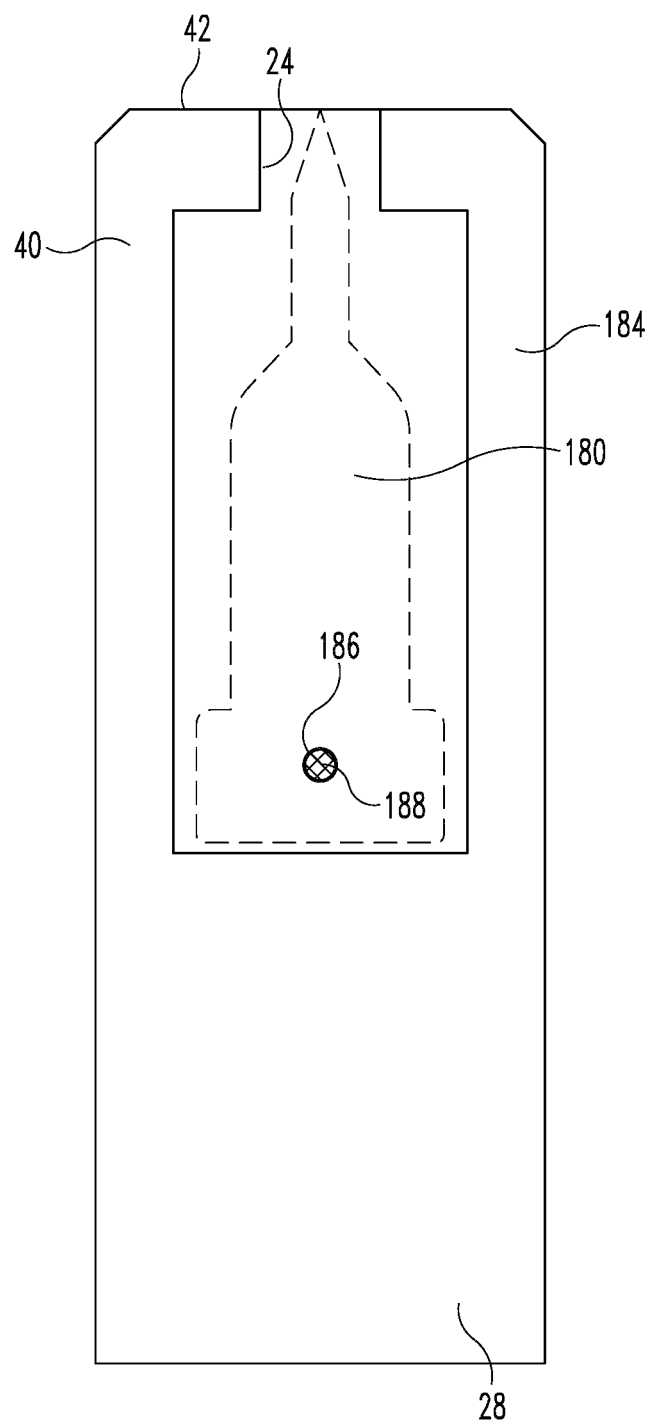
FIG. 7 is a top view of a lancet packet including the FIG. 6 lancet according to one embodiment.

A lancing system according to one embodiment will be described with reference to FIGS. 6 and 7. As can be seen, FIG. 6 illustrates a lancet 180 that shares several features in common with the lancet 30 described above with reference to FIGS. 1-5. For example, the lancet 180 has the body portion 35 with stop edges 36, the neck portion 37, the tip 38, and the engagement opening (notch) or keyhole 142. For the sake of brevity, these common features will not be described in detail below, but reference is made to the previous discussion of these common features in U.S. patent application Ser. No. 11/551,414 filed Oct. 20, 2006, which is hereby incorporated by reference, and the description above. The lancet 180 includes a tack spot 182 to identify the location on the lancet 180 where a portion 188 of sterility sheet 24 is adhered or welded to the lancet 180 as described in more detail below. In the illustrated embodiment, the tack spot 182 is located on the body portion 35. As can be appreciated, the portion 188 of sterility sheet 24 attached to lancet 180 at tack spot 182 immobilizes or locks the lancet 180 prior to use or actuation to avoid damaging the sterility sheet 24. To release the lancet 180 from the sterility sheet 24, a blade or other device pierces the portion 188 of sterility sheet 24 to break the bond or tack weld between sterility sheet 24 and the tack spot 182 of the lancet 180. In another embodiment, the lancet 180 is driven to break the tack weld between sterility sheet 24 and tack spot 182. After the tack weld or bond is broken, movement of the lancet 180 is not impeded by sterility sheet 24 and tack weld 188.

As mentioned previously, the tack spot 182 is located on the lancet 180 to identify the location of attachment between the sterility sheet 24 and the lancet 180. For example, the tack spot 182 could be located on neck portion 37. Furthermore, in other embodiments, one or more tack spots 182 may be located on the lancet 180. As illustrated, tack spot 182 is circular in shape; however, in other embodiments, tack spot 182 may be shaped differently such as rectangular, triangular, or oval to name a few.

As mentioned above, the tack spot 182 is sized, shaped, and positioned on the lancet 180 such that a portion 188 of the sterility sheet 24 is adhered to the lancet 180 at the location of the tack spot 182. The adherence of the portion 188 of the sterility sheet 24 to the lancet 180 immobilizes the lancet 180 within lancet packet 184. One technique of adhering portion 188 of sterility sheet 24 to the lancet 180 is by melting the portion 188 at the location of tack spot 182 onto the lancet 180. In particular, one form of melting the sterility sheet 24 onto the lancet 180 is with a laser.

For purposes of the present embodiment, the underlying principle of laser welding a sterility sheet to a lancet is that for any given type of laser, there are clear (or transparent) materials that will not absorb the energy of the laser (which as a result passes therethrough) and black (or absorptive) materials that will absorb this energy. As will be explained in further detail below, it is important to note that the terms "clear" and "black" refer to the laser-energy absorption characteristics of the materials, and not necessarily to the translucence, opacity or color thereof. In one embodiment, these adjacent clear and black materials are essentially the same chemically as well as physically (e.g. same or nearly the same polymer base, same or nearly the same melting point). In other embodiments, these adjacent clear and black materials are not the same chemically as well as physically. In the embodiment illustrated in FIGS. 6 and 7, the laser would be directed at the clear layer of sterility sheet 24 positioned over the tack spot 182 of lancet 180. The energy of the laser passes through the clear sterility sheet 24 and is absorbed by the black tack spot 182. The black tack spot 182 becomes hot and portion 188 of sterility sheet 24 that corresponds to tack spot 182 in turn melts. The melted portion 188 then cools, leaving a tack weld 186 that adheres sterility sheet 24 to lancet 180. Other techniques of laser welding are discussed below.

Another technique of melting portion 188 onto lancet 180 is with a hot pin. The hot pin applies heat to the sterility sheet 24 at the location of the tack spot 182 to melt the portion 188 and form the tack weld 186 between sterility sheet 24 and lancet 180.

In one form, the tack spot 182 is created on the surface of the lancet 180 by chemically etching the surface. In other forms, the tack spot 182 can be formed by other techniques, such as painting a portion of the surface of the lancet 180, printing a dark spot on the surface of the lancet 180, applying an adhesive marker to a portion of the surface of the lancet 180, and/or burning or scorching a portion of the surface of the lancet 180. Typically, the size and shape of the tack weld 186 corresponds with the size and shape of the tack spot 182. The tack weld 186 can be sized to depend on an amount of sheer force required to break the adhesion between the tack weld 186 and the lancet 180 to release the lancet 180 from the sterility sheet 24. For example, a larger sized tack weld 186 requires a greater force to release the lancet 180 from the sterility sheet 24 as compared to the force required to break a smaller sized tack weld 186.

Figure 8:
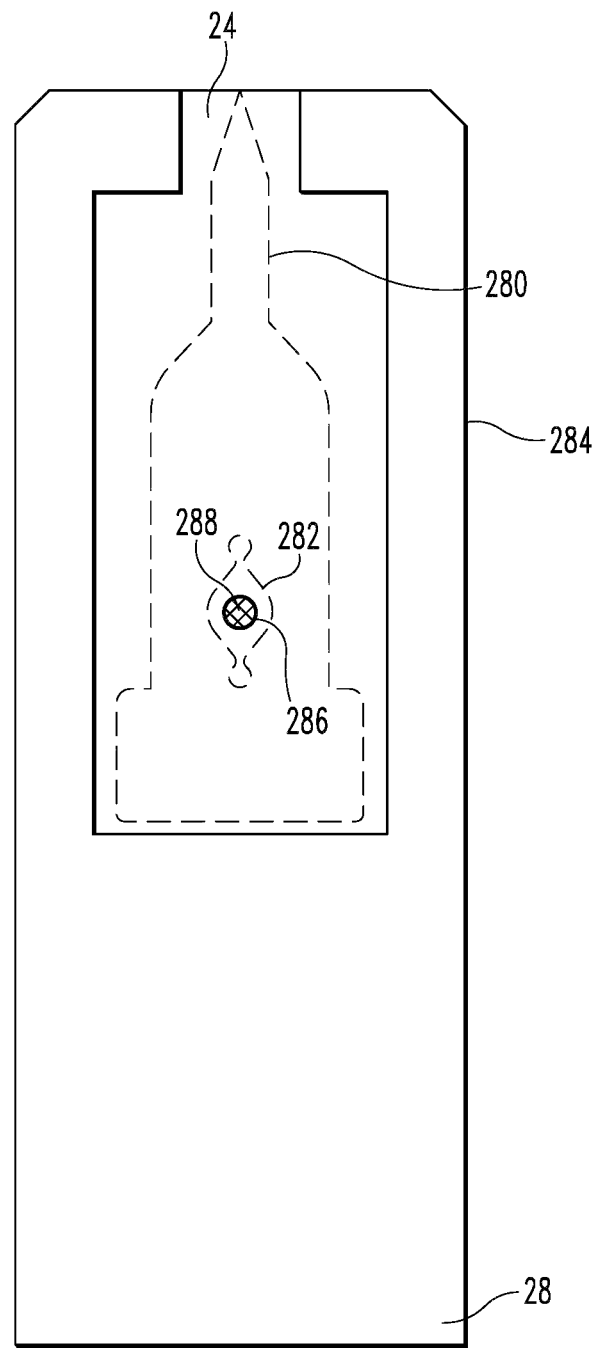
FIG. 8 is a top view of a lancet packet according to another embodiment.

A lancing system according to another embodiment is described with reference to FIGS. 8 and 9. FIG. 8 illustrates a lancet 280 that shares several features in common with the lancet 30 and the lancet 180 described above with reference to FIGS. 1 and 6, respectively. Lancet 280 defines an engagement opening 282 similar to engagement opening 142 of lancet 180. For the sake of brevity, these common features will not be described in detail below but reference is made to the previous discussion of these common features. As described previously, lancet 280 is placed within guide member 28. The sterility sheet 24 is folded over the lancet 280 and guide member 28 to form a lancet packet 284.

Figure 9:
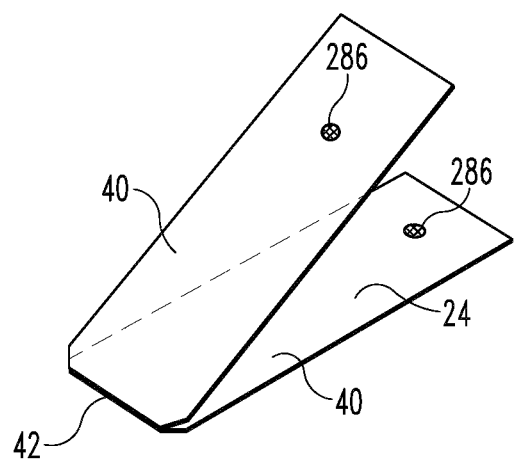
FIG. 9 is a perspective view of the sterility sheet from the FIG. 8 embodiment.

As illustrated in FIGS. 8 and 9, the sterility sheet 24 includes a tack spot 286 positioned over the engagement opening 282 of lancet 280 when the lancet 280 is enclosed within the sterility sheet 24. In this form, tack spot 286 forms a shape on each of the flaps 40 of the sterility sheet, as illustrated in FIG. 9. The tack spot 286 is similar to the tack spot 182 described above; however, the tack spot 286 is located on sterility sheet 24. The tack spot 286 can be any shape or size.

In one form, the tack spots 286 are melted so that the flaps 40 are pulled through the engagement opening 282 to pinch the flaps 40 together through the engagement opening 282. As the melted tack spots 286 of flaps 40 cool, a tack weld 288 is formed to limit movement of the lancet 280 in the lancet packet 284. If the lancet 280 moves, for example during shipment or prior to use of the lancet 280, the tack weld 288 limits movement of the lancet 280 within the lancet packet 284 such that the lancet 280 does not pierce the sterility sheet 24. To form an incision in skin, a blade or other piercing mechanism pierces the tack weld 288 to break the bond between the flaps 40 and separate the flaps 40. In another embodiment, the lancet 280 is actuated with enough force to break the tack weld 288 and separate the flaps 40. In either embodiment, after the tack weld 288 is pierced or broken, the flaps 40 of sterility sheet 24 no longer impede movement of the lancet 280.

In particular, one form of melting the tack spots 286 on the flaps 40 is with a laser. For the purposes of the present embodiment, the underlying principle of laser welding two sterility sheets together is that for any given type of laser, there are clear (or transparent) materials that will not absorb the energy of the laser (which as a result passes therethrough) and black (or absorptive) materials that will absorb this energy. As explained previously, it is important to note that the terms "clear" and "black" refer to the laser-energy absorption characteristics of the materials, and not necessarily to the translucence, opacity or color thereof. In one embodiment, these adjacent clear and black materials are essentially the same chemically as well as physically (e.g. same or nearly the same polymer base, same or nearly the same melting point). In the embodiment illustrated in FIGS. 8 and 9, the laser beam is directed at tack spots 286 of sterility sheet 24 positioned over the engagement opening 282 of lancet 280. A laser beam can be directed at each of the tack spots 286 and applied to both tack spots either sequentially or simultaneously. Tack spots 286 absorb the energy of the laser. The tack spot 286 of sterility sheet 24 becomes hot and melts. The melted tack spot 286 then cools, leaving a tack weld 288 that adheres flaps 40 of sterility sheet 24 to each other through the engagement opening 282.

In one embodiment, the melting of flaps 40 does not occur through the entire thickness of either flap 40. That is, the black tack spot 286 is typically only melted to a certain depth therein for a given laser energy.

Another technique of melting tack spots 286 and pulling flaps 40 through engagement opening 282 of lancet 280 is with a hot pin. The hot pin applies heat to the sterility sheet 24 at the location of the tack spots 286 to melt the flaps 40 and form the tack weld 288 that pinches and pulls flaps 40 through engagement opening 282 of lancet 280.

The tack weld 288 typically corresponds to the shape and size of the tack spot 286. In one embodiment, the tack weld 288 does not exceed the overall thickness of the lancet 280. In this embodiment, since the tack weld 288 does not exceed the overall thickness of lancet 280, additional lancet packets 284 can be stacked in a cartridge or meter.

Figure 10:
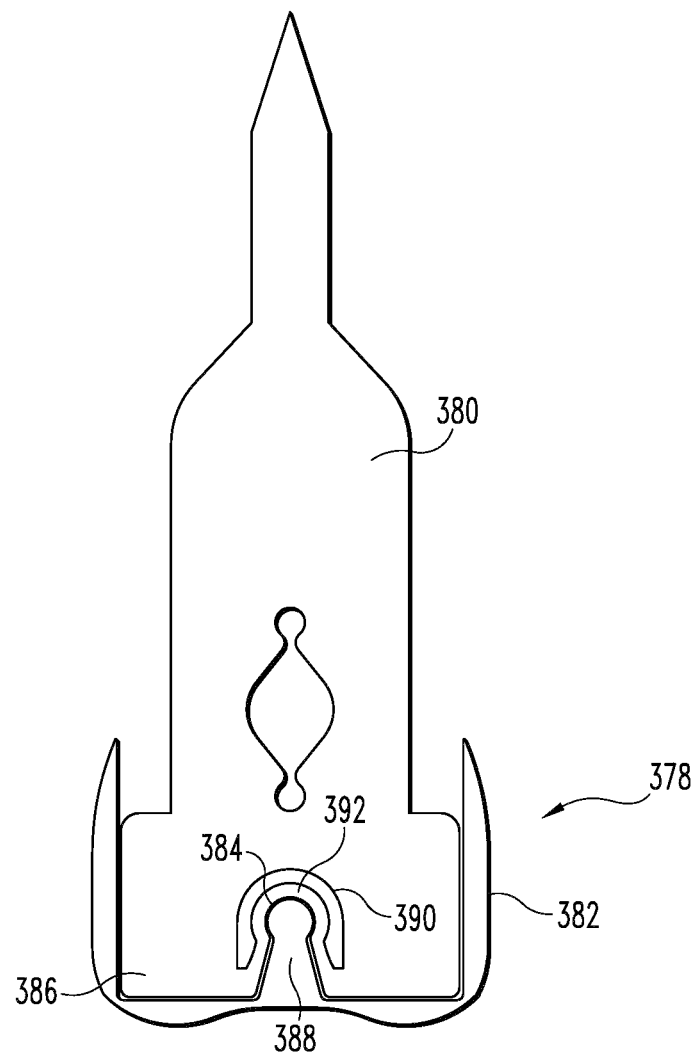
FIG. 10 is a top view of a locking mechanism according to one embodiment.

Another embodiment shown in FIG. 10 illustrates a locking mechanism 378 for releasably restraining movement of a lancet 380. Locking mechanism 378 includes a lancet 380 releasably immobilized by a spacer 382. The lancet 380 is similar to lancet 180 described above. In another form, lancet 380 and spacer 382 are coupled with a test strip 26. Additionally, the lancet 380 and spacer 382 can be enclosed within a sterility sheet 24 to form a lancet packet, as described above. In this embodiment, lancet 380 is releasably immobilized by the spacer 382 to maintain integrity of sterility sheet 24 prior to actuation of the lancet 380 and disengagement of lancet 380 from the spacer 382. Lancet 380 defines a receiving end 384 at a base end 386. Spacer 382 includes an insertion portion 388 to connect with receiving end 384 of lancet 380 to retain or lock lancet 380 with spacer 382. Receiving end 384 and insertion portion 388 are similarly sized and complementarily shaped such that insertion portion 388 and receiving end 384 mate together. In the illustrated embodiment, receiving end 384 forms a keyway shape and insertion portion 388 forms a corresponding key shape. Receiving end 384 and insertion portion 388 are also configured such that receiving end 384 releases insertion portion 388 the lancet 380 or the spacer 382 are forcibly separated.

Base end 386 defines a relief slot 390 adjacent a deformable portion 392. As the insertion portion 388 is inserted into or removed from receiving end 384, the deformable portion 392 and the relief slot 390 deform as necessary. As the deformable portion 392 and the relief slot 390 deform, the user holding the lancet 380 will feel a tactile sensation and/or hear an audible sound which gives the locking mechanism 378 a spring-like property. Moreover, after use of the lancet 380, the insertion portion 388 can be reinserted into the receiving end 384 to immobilize the lancet 380 with the spacer 382. Reattachment of the lancet 380 with the spacer 382 in a lancet packet reduces the chance that a person will be accidentally stuck from a used lancet 380. In one embodiment, the receiving end 384 is formed by chemically etching the surface of the lancet 402.

Figure 11:
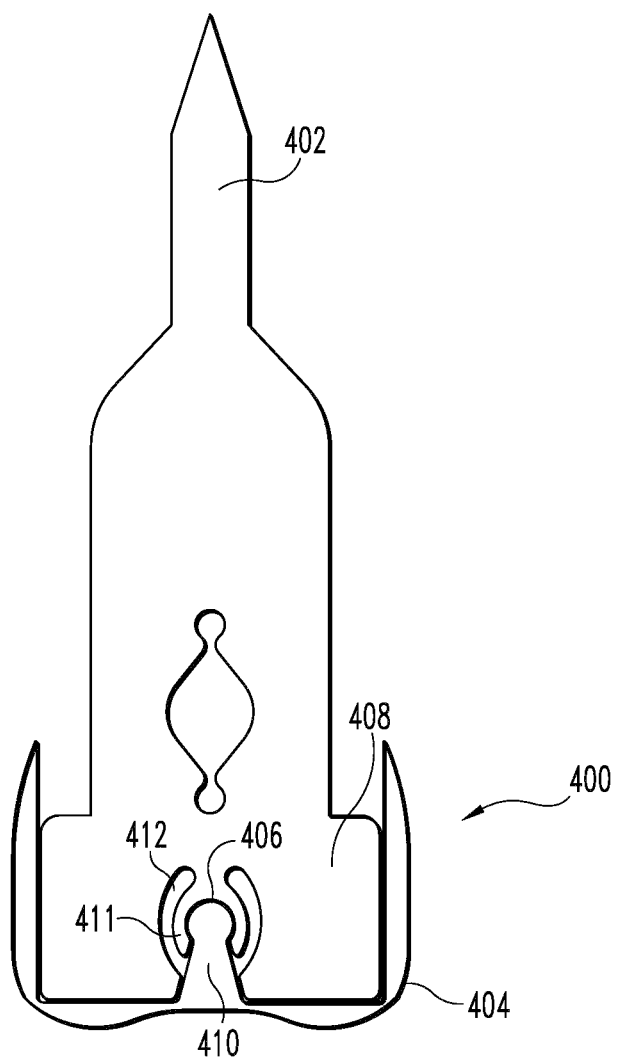
FIG. 11 is a top view of a locking mechanism according to a second embodiment.

In another embodiment, a locking mechanism 400 having a lancet 402 releasably immobilized by a spacer 404 is illustrated in FIG. 11. Locking mechanism 400 is similar to locking mechanism 378. Locking mechanism 400 includes a lancet 402 and a spacer 404. Lancet 402 is similar to lancet 180 described above. For the sake of brevity, similar features of lancet 402 as compared to lancet 180 are not described below. The lancet 402 defines a receiving end 406 at a base end 408. Receiving end 406 is similar to receiving end 384. Spacer 404 includes an insertion portion 410. Insertion portion 410 is similar to insertion portion 388. In the illustrated embodiment, the insertion portion 410 forms a key shape and the receiving end 406 forms a corresponding keyway shape. In other embodiments, insertion portion 410 and receiving end 406 are shaped differently but are still complementary to each other. Base end 408 includes a deformable portion 411 positioned between the relief slots 412 and the insertion portion 410. However, receiving end 406 includes a deformable portion 411 positioned between a pair of relief slots 412. As illustrated, each of the slots 412 flairs from the keyway shape of the receiving end 406. Moreover, each of the slots 412 is an arc or crescent shape; however, in other embodiments the slots 412 may be shaped differently. As the insertion portion 410 is inserted into the receiving end 406, the deformable portion 411 and the relief slots 412 deform so the user hears an audible sound and/or feels a tactile sensation that gives the locking mechanism 400 a spring-like property. After the lancet 402 is used, the movement of lancet 402 relative to spacer 404 can be immobilized. For example, insertion portion 410 is inserted into the receiving end 406 to lock the lancet 402 with the spacer 404, thereby limiting movement of the lancet 402 and preventing accidental sticks with the used lancet 402. Movement of the lancet 402 is immobilized after the lancet 402 is re-attached to the spacer 404 to avoid unintentional movement of the lancet 402 away from the spacer 404.

Figure 12:
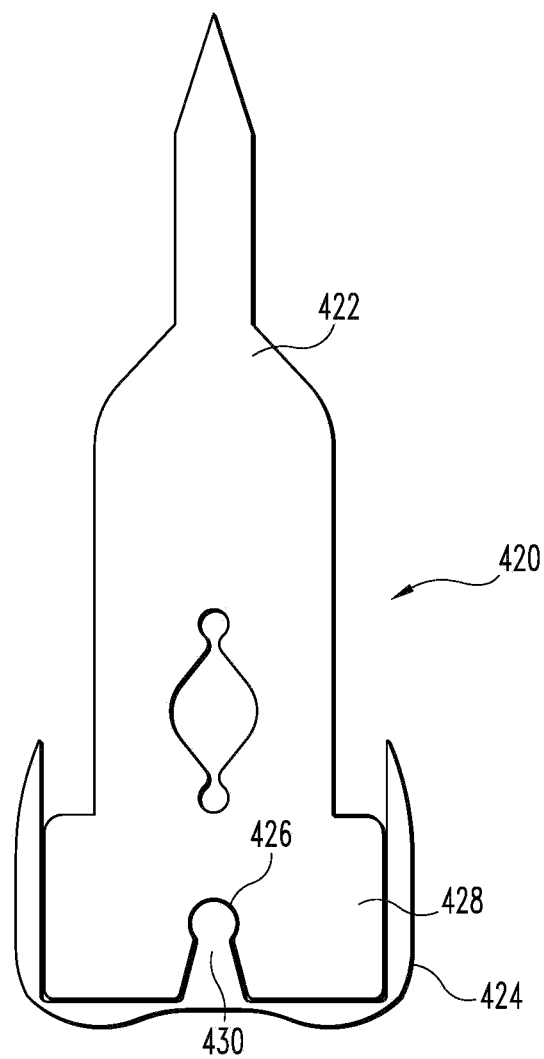
FIG. 12 is a top view of a locking mechanism according to a third embodiment.

A locking mechanism 420 having a lancet 422 releasably immobilized by a spacer 424 is illustrated in FIG. 12. Lancet 422 is similar to lancet 180 described above. For the sake of brevity, similar features of lancet 422 as compared to lancet 180 are not described below. Lancet 422 defines a receiving end 426 at a base end 428. Spacer 424 includes an insertion portion 430 to insert into receiving end 426 of lancet 422. Receiving end 426 and insertion portion 430 are similarly sized and complementarily shaped such that insertion portion 430 is inserted and retained in receiving end 426. In the illustrated embodiment, receiving end 426 has a keyway shape and insertion portion 430 has a corresponding key shape. In other embodiments, receiving end 426 and insertion portion 430 are shaped differently but still releasably lock together.

Figure 13:
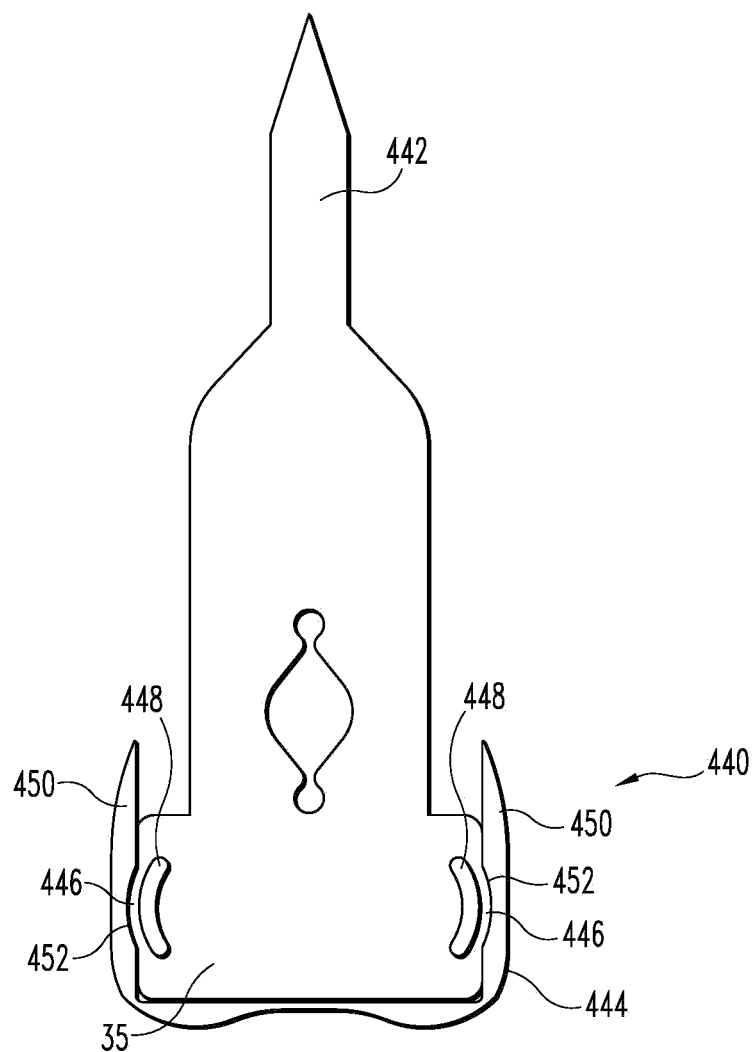
FIG. 13 is a top view of a locking mechanism according to a fourth embodiment.

Locking mechanism 440 including a lancet 442 releasably immobilized by a spacer 444 is illustrated in FIG. 13. Lancet 442 is similar to lancet 180 described above. For the sake of brevity, similar features of lancet 442 as compared to lancet 180 are not described below. Lancet 442 includes a body portion 35 having a pair of protruding sides 446 for connecting with the spacer 444 as described below. Each of the protruding sides 446 is curved in shape and bulges out from body portion 35. In other embodiments, each of the protruding sides 446 can be shaped differently from each other or similar to each other. Body portion 35 of lancet 442 also includes a pair of relief slots 448 near the protruding sides 446. As illustrated, each of the relief slots 448 has a crescent shape with a similar curvature as the protruding sides 446. In other embodiments, the relief slots 448 may be shaped differently. In one form, the relief slots 448 are formed by chemically etching the lancet 442.

As shown in FIG. 13, spacer 444 includes a pair of legs 450. Each of the pair of legs 450 defines a recess 452 having a similar size and complementary shape as protruding side 446 such that protruding side 446 nests in recess 452 to retain lancet 442 in spacer 444. Relief slots 448 are configured and positioned in the body portion 35 such that the protruding sides 446 and relief slots 448 can deform to give a spring-like property to the lancet 442 and spacer 444 as protruding sides 446 of the lancet 442 are inserted into and/or withdrawn from the recesses 452 of the spacer 444. In one form, legs 450 are configured to bend as protruding sides 446 of the lancet 442 are inserted into and/or withdrawn from recesses 452 of spacer 444. As protruding sides 446 are inserted into and/or withdrawn from recesses 452 the user feels a tactile sensation and/or the user hears an audible sound. As can be appreciated, immobilizing lancet 442 with the spacer 444 in an integrated lancing test strip after the lancet 442 has been used reduces the risk of potentially injuring and/or contaminating someone with the used lancet 442.

Figure 14:
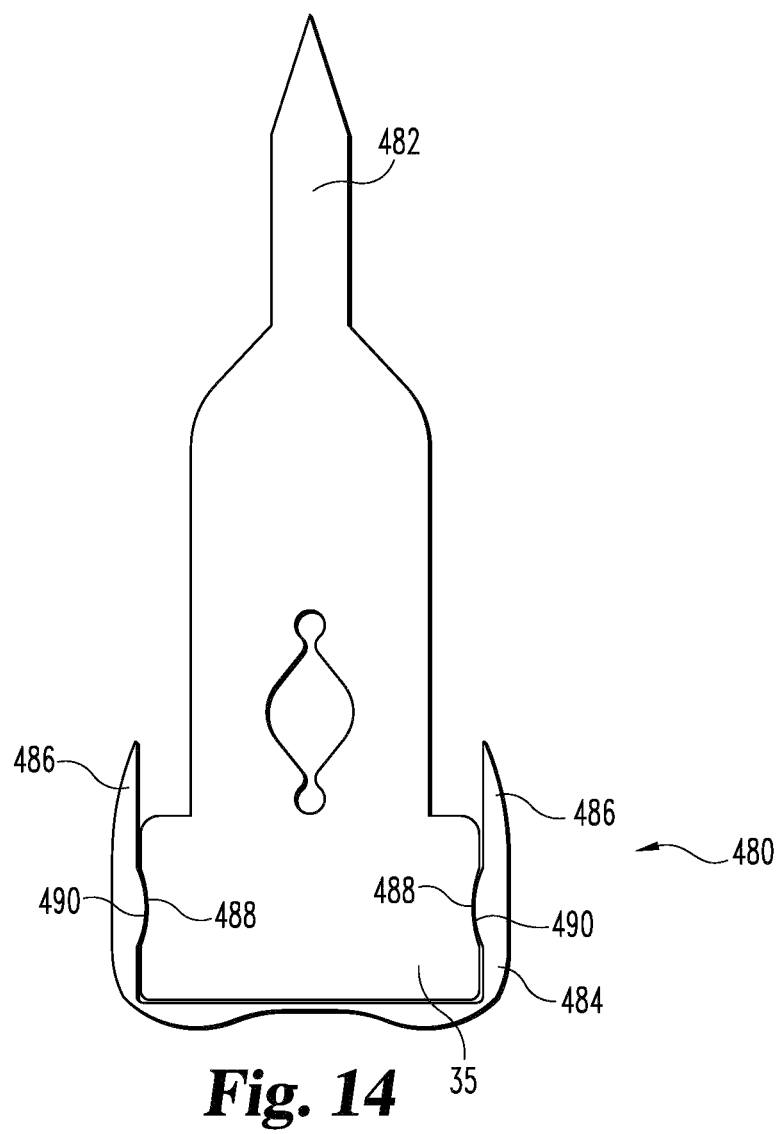
FIG. 14 is a top view of a locking mechanism according to a fifth embodiment.

Another embodiment of a locking mechanism 480 having a lancet 482 releasably immobilized by a spacer 484 is illustrated in FIG. 14. Lancet 482 is similar to lancet 442, and spacer 484 is similar to spacer 444. For the sake of brevity, similar features of lancet 482 and spacer 484 are not described below. Lancet 482 includes a body portion 35 defining a pair of recesses 488 for receiving and releasably retaining protruding sides 490 of the spacer 444 as described below. Each of the recesses 488 has a curved shape and forms a depression in body portion 35. In other embodiments, recesses 488 can be shaped differently.

Spacer 484 includes a pair of legs 486, each leg 486 having a protruding side 490. Each of the protruding sides 490 has a curved shape that is similarly sized and complementarily shaped as recess 488 such that protruding side 490 nests in recess 488. The nesting of protruding side 490 with recess 488 releasably immobilizes the lancet 482 with the spacer 484. In this embodiment, legs 486 are configured to bend as body portion 35 of the lancet 482 is inserted into and/or withdrawn from spacer 484 such that the user feels a tactile sensation and/or the user hears an audible sound. As can be appreciated, immobilizing lancet 482 with the spacer 484 in an integrated lancing test strip after the lancet 482 is used reduces the risk of potentially injuring and/or contaminating someone with the used lancet 482.

Figure 15:
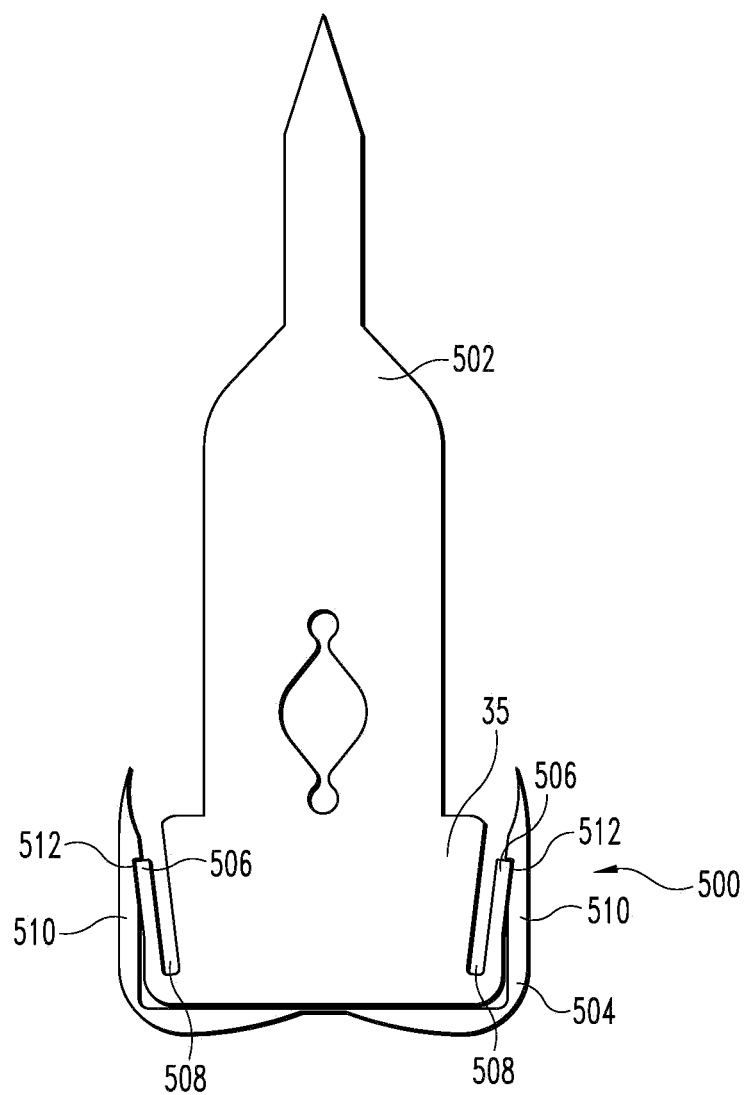
FIG. 15 is a top view of a locking mechanism according to a sixth embodiment.

Another embodiment of a locking mechanism 500 is illustrated in FIG. 15. In this embodiment, the locking mechanism 500 includes a used lancet 502 connected with a spacer 504. In this embodiment, prior to actuation of an unused or sterile lancet 502, the sterile lancet 502 is releasably immobilized by sterility sheet 24 as shown in FIGS. 6, 7, 8 and/or 9, and described previously. After the lancet 502 forms an incision in skin, the lancet 502 is retracted into the guide slot or opening 31 and immobilized by spacer 504 as described below. Spacer 504 is configured to retain lancet 502 after lancet 502 has been contaminated to prevent re-use of lancet 502. The lancet 502 includes a body portion 35 having a pair of insertion legs 506. Body portion 35 of lancet 502 also defines a pair of slots 508, each slot 508 located adjacent each of the legs 506. The spacer 504 includes a pair of receiver legs 510. Each of the receiver legs 510 defines a receiver slot 512 sized and shaped to retain one of the insertion legs 506 to limit the movement of lancet 502 when the lancet 502 is connected with the spacer 504. A portion of each of the legs 506 fits in one of the receiver slots 512 to retain lancet 502 in spacer 504. In this embodiment, the configuration of insertion legs 506 and receiver slots 512 secure the lancet 502 to the spacer 504 after use of the lancet 502 to avoid re-use of a contaminated lancet 502.

Figure 16:
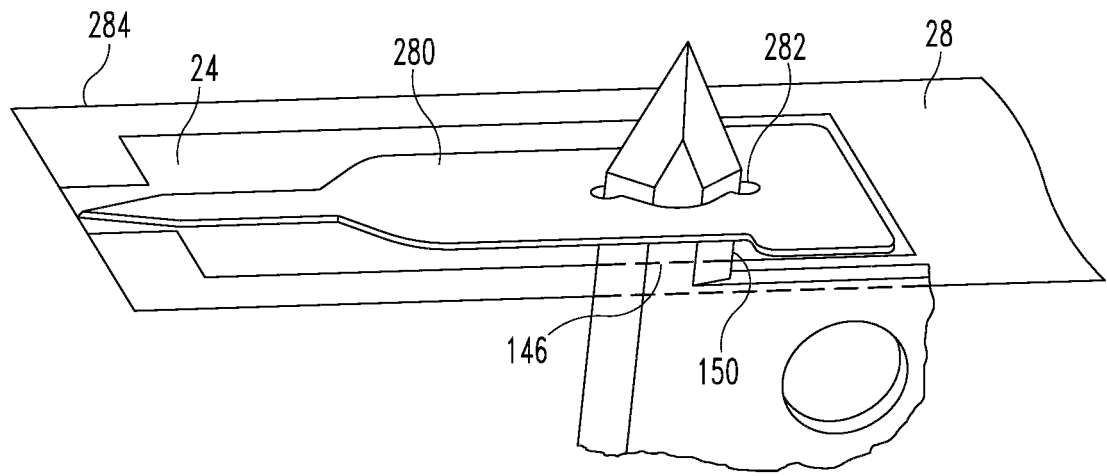
FIG. 16 is a perspective view of the FIG. 8 lancet packet engaged to an engagement blade of a firing mechanism.
Figure 17:
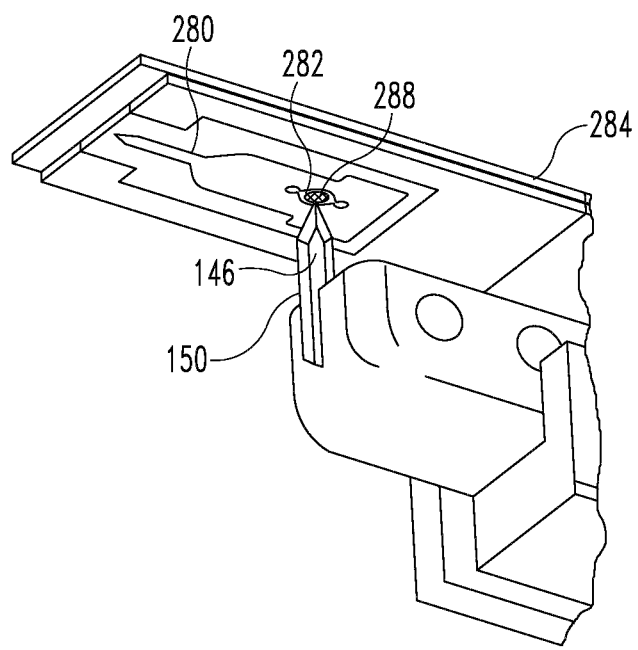
FIG. 17 is a perspective view of an integrated disposable that incorporates the FIG. 8 lancet packet when loaded in a meter prior to firing of the lancet.

FIGS. 16 and 17 illustrate a blade 146 of a firing mechanism engaging the engagement opening 282 in the lancet 280. FIGS. 16 and 17 illustrate blade 146 of a firing mechanism and for the sake of brevity these common features will not be described in detail below, but reference is made to the previous discussion of these common features described in U.S. patent application Ser. No. 11/551,414, filed Oct. 20, 2006, entitled "SYSTEM AND METHOD FOR BREAKING A STERILITY SEAL TO ENGAGE A LANCET", which is hereby incorporated by reference. The blade 146 in the depicted embodiment is a dual edge blade with opposing cutting edges 150 that are configured to cut a travel path or slit in the tack weld 288 during firing of the lancet 280. In the illustrated embodiment, the blade 146 pierces through the tack weld 288 of the lancet packet 284 to break the tack weld 288. After the tack weld 288 is pierced, the broken tack weld 288 no longer impedes movement of the lancet 280. In another embodiment, the lancet 280 is actuated with enough force to break through the tack weld 288. In either embodiment, the broken tack weld 288 no longer impedes movement of the lancet 280.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:
1. An integrated disposable, comprising:
a test sensor configured to analyze body fluid; and
a lancet packet coupled to the test sensor, the lancet packet including:
a cover foil folded into two flaps,
a lancet disposed between the two flaps of the cover foil wherein the cover foil covers at least a lancet tip of the lancet, and
the cover foil including a hot tack weld that contacts the lancet, wherein the hot tack weld welds to the lancet to immobilize the lancet within the lancet packet.

2. The integrated disposable of claim 1, wherein the hot tack weld secures the cover foil to the lancet.

3. The integrated disposable of claim 1, wherein:
the lancet defines an opening; and
the hot tack weld pinches and welds opposing sheets of the cover foil together through the opening in the lancet.

4. The integrated disposable of claim 1, further comprising:
a locking mechanism configured to retain the lancet within the lancet packet after the lancet is actuated.

5. The integrated disposable of claim 4, further comprising:
the hot tack weld being configured to immobilize the lancet prior to actuation of the lancet;
the locking mechanism including a spacer; and
one of the lancet or the spacer including an insertion portion and the other of the lancet or spacer defining a receiving end, the insertion portion and the receiving end having complimentary shapes sized to attach the lancet to the spacer after the lancet is actuated.

6. The integrated disposable of claim 1, wherein the cover foil includes a tack spot positioned over the opening in the lancet, wherein the tack spot is melted to form the hot tack weld.

7. A method, comprising:
covering at least a lancet tip of a lancet with a cover foil folded into two layers to form a lancet packet by placing at least the lancet tip between the layers; and
melting a portion of the cover foil to form a hot tack weld that contacts the lancet, wherein the hot tack weld welds to the lancet to immobilize the lancet.

8. The method of claim 7, further comprising:
forming an integrated disposable by coupling the lancet packet to a test element configured to analyze body fluid.

9. The method of claim 7, wherein the melting the portion of the cover foil includes laser welding the portion of the cover foil to the lancet to form the hot tack weld.

10. The method of claim 7, further comprising:
the hot tack weld being configured to immobilize the lancet prior to actuation of the lancet; and
forming a locking mechanism on the lancet that immobilizes the lancet after the lancet is actuated.

11. The method of claim 7, further comprising:
sterilizing the lancet; and
attaching the lancet packet to a test element to form an integrated disposable.

12. The method of claim 7, further comprising:
pinching together opposing sheets of the cover foil through an engagement opening of the lancet; and
wherein the melting the portion of the cover foil includes melting the pinched portions of the opposing sheets to form the hot tack weld.

13. An apparatus, comprising:
a spacer; and
a lancet having a lancet tip and a lancet body, wherein one of the lancet body or the spacer includes an insertion portion and the other of the lancet body or the spacer defines a receiving end, the insertion portion and the receiving end having complementary and deformable shapes to releasably lock the lancet body to the spacer;
wherein the lancet body defines a relief slot that extends through the lancet body, wherein the relief slot is configured to form a deformable portion adjacent the relief slot in the lancet body, wherein the relief slot and the deformable portion deform as the lancet body locks with the spacer.

14. The apparatus of claim 13, further comprising:
the lancet and the spacer attached to a test element to form an integrated disposable.

15. The apparatus of claim 13, further comprising:
a cover foil being configured to cover at least the lancet tip, the cover foil including a hot tack weld configured to immobilize the lancet prior to actuation of the lancet; and
the insertion portion inserted into the receiving end to releasably lock the lancet to the spacer after actuation of the lancet.

16. A method, comprising:
releasing a lancet immobilized by a first hot tack weld to the lancet and a top cover foil and a second hot tack weld to the lancet and a bottom cover foil by breaking the first and second hot tack welds by moving the lancet relative to the top and bottom cover foils.

17. The method of claim 16, further comprising:
the breaking the first and second hot tack welds includes piercing the cover foil at the first and second hot tack welds with a firing mechanism.

18. The method of claim 16, further comprising:
analyzing a bodily fluid with a test sensor that is attached to the lancet to form an integrated disposable.

19. The method of claim 18, further comprising:
inserting the integrated disposable into a meter.

20. A method, comprising:
disengaging a lancet from a spacer for unimpeded movement of the lancet relative to the spacer, wherein one of the lancet or the spacer includes an insertion portion and the other of the lancet or the spacer defines a receiving end, the insertion portion and the receiving end having complementary shapes to releasably lock the lancet to the spacer, the lancet having a lancet tip and a lancet body, the lancet body defines a relief slot that extends through the lancet body, wherein the relief slot is configured to form a deformable portion adjacent the relief slot in the lancet body;
extending the lancet away from the spacer as the insertion portion and the receiving end are deformed to release the lancet from the spacer; and
re-engaging the insertion portion with the receiving end to immobilize the lancet relative to the spacer while deforming the relief slot and the deformable portion.

21. The method of claim 20, further comprising:
attaching a test element to the lancet to form an integrated disposable.

* * * * *